(12) United States Patent
Yada et al.

(10) Patent No.: US 7,015,357 B2
(45) Date of Patent: Mar. 21, 2006

(54) PROCESSES FOR PRODUCING (METH)ACRYLIC ACID

(75) Inventors: Shuhei Yada, Yokkaichi (JP); Kenji Takasaki, Yokkaichi (JP); Yasushi Ogawa, Yokkaichi (JP); Yoshiro Suzuki, Yokkaichi (JP)

(73) Assignee: Mitsubishi Chemical Corporation, Tokyo (JP)

( * ) Notice: Subject to any disclaimer, the term of this patent is extended or adjusted under 35 U.S.C. 154(b) by 0 days.

(21) Appl. No.: 10/898,341

(22) Filed: Jul. 26, 2004

(65) Prior Publication Data

US 2005/0004396 A1 Jan. 6, 2005

Related U.S. Application Data

(63) Continuation of application No. PCT/JP03/00837, filed on Jan. 29, 2003.

(30) Foreign Application Priority Data

Jan. 29, 2002 (JP) .............................. 2002-020328

(51) Int. Cl.
*C07C 51/42* (2006.01)
*C07C 57/02* (2006.01)

(52) U.S. Cl. ...................................... 562/600; 562/598
(58) Field of Classification Search ................ 562/598
See application file for complete search history.

(56) References Cited

U.S. PATENT DOCUMENTS 5,856,562 A * 1/1999 Mine et al. .................. 560/205

6,448,438 B1 9/2002 Yada et al.

FOREIGN PATENT DOCUMENTS

| EP | 1 035 103 | 9/2000 |
|---|---|---|
| EP | 1 116 709 | 7/2001 |
| JP | 7-228548 | 8/1995 |
| JP | 7-252477 | 10/1995 |
| JP | 8-239341 | 9/1996 |
| JP | 10-175912 | 6/1998 |

* cited by examiner

*Primary Examiner*—Paul A. Zucker
(74) *Attorney, Agent, or Firm*—Oblon, Spivak, McClelland, Maier & Neustadt, P.C.

(57) ABSTRACT

In the purification and distillation step of acrylic acid (including (meth)acrylic acid), stable continuous operation for a long period is enabled by inhibiting the undesirable polymerization reaction of acrylic acid thereby to prevent the device from a trouble such as clogging. A process for producing acrylic acid which comprises purifying crude acrylic acid prepared by vapor-phase catalytic oxidation by distillation, wherein the concentration of β-acryloxypropionic acid in the feed stream to a distillation column mainly for the separation of water from acrylic acid is controlled to be at most one-fiftieth of the concentration of acrylic acid; the concentration of β-acryloxypropionic acid in the feed stream to a distillation column mainly for the separation of acetic acid from acrylic acid is controlled to be at most one-fortieth of the concentration of acrylic acid; and the concentration of β-acryloxypropionic acid in the feed stream to a distillation column mainly for the separation of acrylic acid from water, acetic acid and a solvent is controlled to be at most one-fiftieth of the concentration of acrylic acid.

8 Claims, 2 Drawing Sheets

PROCESSES FOR PRODUCING (METH)ACRYLIC ACID

BACKGROUND OF THE INVENTION

1. Field of the Invention

The present invention relates to processes for producing (meth)acrylic acid. Particularly, the present invention relates to processes for producing (meth)acrylic acid of a high purity constantly by continuous distillation and purification of crude (meth)acrylic acid obtained by vapor-phase catalytic oxidation.

In this specification, "(meth)acrylic acid" is a general term for acrylic acid and methacrylic acid, and it may be either one or both of them.

2. Discussion of Background

Acrylic acid is industrially important as a raw material for a resin with high water absorbability and further, as a raw material for various acrylic esters. Recently, it is produced by a vapor-phase catalytic oxidation reaction of propylene.

In processes to obtain acrylic acid by oxidizing propylene, conditions for oxidation to acrolein and oxidation to acrylic acid in the next step are different. Accordingly, there is a two step oxidation process in which the respective steps are carried out in separate reactors and a process in which oxidization is proceeded directly to acrylic acid in one step. An acrylic acid-containing gas obtained by such a vapor-phase catalytic oxidation reaction, is contacted with water in a collection column (condensation column) to obtain an aqueous acrylic acid solution, which is extracted in an extraction column by adding a suitable extraction solvent, whereupon the extraction solvent is separated in a solvent separation column. Then, acetic acid is separated in an acetic acid separation column, and further, a byproduct is separated in a fractionating column to obtain a purified product of acrylic acid.

Further, in recent years, instead of a solvent extraction method wherein recovery of acrylic acid from the above aqueous acrylic acid solution is carried out by means of an extraction solvent, an azeotropic separation method is carried out wherein distillation is carried out by means of water and an azeotropic solvent, as show in the after-mentioned FIGS. 1 and 2, so that from the top of an azeotropic separation column, an azeotropic mixture comprising water and the azeotropic solvent, is distilled, and from the bottom, acrylic acid is recovered.

Acrylic acid has a very high polymerizability, and a solid substance is frequently formed by a polymerization reaction in the step of distillation and purification, whereby a trouble such as clogging of devices takes place, which tends to hinder a constant continuous operation. Therefore, by adding a polymerization inhibiter (such as hydroquinone, phenothiazine, copper dithiocarbamate, an n-oxyl compound or air) and by decreasing hot sections and retention sections to the minimum, ingenuities in the operation and device are carried out to suppress such an undesirable polymerization reaction. (Acrylic Acid and Polymer Thereof [I]: published by Shokodo Co. Ltd., JP-A-7-252477, JP-A-7-228548, JP-A-10-175912, JP-A-8-239341)

However, it is insufficient to suppress the polymerization in the purification step of acrylic acid by such a countermeasure alone. Accordingly, it is desired to develop a technique, whereby polymerization of acrylic acid can more certainly be prevented so as to accomplish a constant continuous operation.

Further, heretofore, in order to prevent the polymerization of acrylic acid, various studies have been made as mentioned above. However, it has not been reported that an adduct of two molecules of (meth)acrylic acid, such as a β-acryloxypropionic acid or a β-methacryloxyisobutyric acid, of which the concentration is to be reduced by the present invention, is involved in a polymerization trouble in the step of distillation and purification of (meth)acrylic acid.

It is an object of the present invention to provide a process for producing (meth)acrylic acid, whereby the undesired polymerization reaction of (meth)acrylic acid in a step of distillation and purification of (meth)acrylic acid is suppressed, a trouble such as clogging of devices is avoided, and a constant continuous operation can be carried out for a long period of time.

SUMMARY OF THE INVENTION

The present inventors have conducted various studies to accomplish the above objects, and as a result, have found that an adduct of two molecules of (meth)acrylic acid by-produced during the production of (meth)acrylic acids is largely involved in the polymerization trouble of (meth)acrylic acid in the step of distillation and purification, and a constant continuous operation can be carried out without having a polymerization trouble by controlling the concentration of the adduct of two molecules of (meth)acrylic acid in the feed stream fed to a distillation column to be not higher than a certain specific level.

Namely, the present invention is essentially directed to the following.

(1) A process for producing (meth)acrylic acid, which comprises a step of feeding crude (meth)acrylic acid obtained by vapor phase catalytic oxidation, to a distillation column mainly for the separation of water and (meth)acrylic acid, to separate water, wherein the concentration by mass of an adduct of two molecules of (meth)acrylic acid in the feed stream to the distillation column is controlled to be one-fiftieth of the concentration by mass of (meth)acrylic acid in the feed stream.

(2) A process for producing (meth)acrylic acid, which comprises a step of feeding crude (meth)acrylic acid obtained by vapor phase catalytic oxidation, to a distillation column mainly for the separation of (meth)acrylic acid and acetic acid, to separate acetic acid, wherein the concentration by mass of an adduct of two molecules of (meth)acrylic acid in the feed stream to the distillation column is controlled to be one-fortieth of the concentration by mass of (meth)acrylic acid in the feed stream.

(3) A process for producing (meth)acrylic acid, which comprises a step of feeding crude (meth)acrylic acid obtained by vapor phase catalytic oxidation, to a distillation column mainly for the separation of water, acetic acid and a solvent, and (meth)acrylic acid, to separate water, acetic acid and the solvent, wherein the concentration by mass of an adduct of two molecules of (meth)acrylic acid in the feed stream to the distillation column is controlled to be one-fiftieth of the concentration by mass of (meth)acrylic acid in the feed stream.

(4) The process for producing (meth)acrylic acid according to any one of (1) to (3), wherein the feed liquid contains a liquid of an off specification tank.

(5) The process for producing (meth)acrylic acid according to (4), wherein the concentration by mass of the adduct of two molecules of (meth)acrylic acid in the off specification tank is at most 5%.

DETAILED DESCRIPTION OF THE PREFERRED EMBODIMENTS

In the present invention, as an impurity which is present in the step of distillation and purification of acrylic acid, as a low boiling point impurity, formaldehyde, acetaldehyde, propionaldehyde, acrolein, formic acid, acetic acid, an azeotropic solvent or water may, for example, be mentioned. Further, as a high boiling point impurity, propionic acid, crotonic acid, benzaldehyde, furfural, benzoic acid, phenol, β-hydroxypropionic acid, β-acryloxypropionic acid or a polymerization inhibitor may, for example, be mentioned.

Among such many impurities, the impurity, of which the concentration is to be controlled in the present invention, is an adduct of two molecules of acrylic acid, namely, β-acryloxypropionic acid. The β-acryloxypropionic acid is produced by the Michael addition reaction of another acrylic acid with an acryl group of acrylic acid as represented by the following reaction formula (hereinafter this adduct of two molecules of acrylic acid will be sometimes referred to as "acrylic acid dimer").

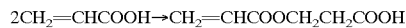

The reason why the acrylic acid dimmer is largely involved in the polymerization trouble of acrylic acid is not clearly understood. However, from studies by the present inventors, it has been found that acrylic acid will readily polymerize and insoluble polymerization materials will increase as the concentration of β-acryloxypropionic acid contained of the feed stream in the distillation column will increase.

Further, the adduct of two molecules of methacrylic acid by-produced during the production of methacrylic acid is β-methacryloxyisobutyric acid produced by the following dimerization reaction.

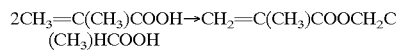

The present invention also includes cases to feed to a distillation column a liquid stored in a buffer tank, an off specification tank, a rundown tank or the like, as will be described hereinafter. Among them, particularly, in a case where a liquid in the off specification tank is contained in the feed stream, the concentration by mass of the adduct of two molecules of (meth)acrylic acid in the off specification tank is preferably at most 5 mass %.

Figure 1:
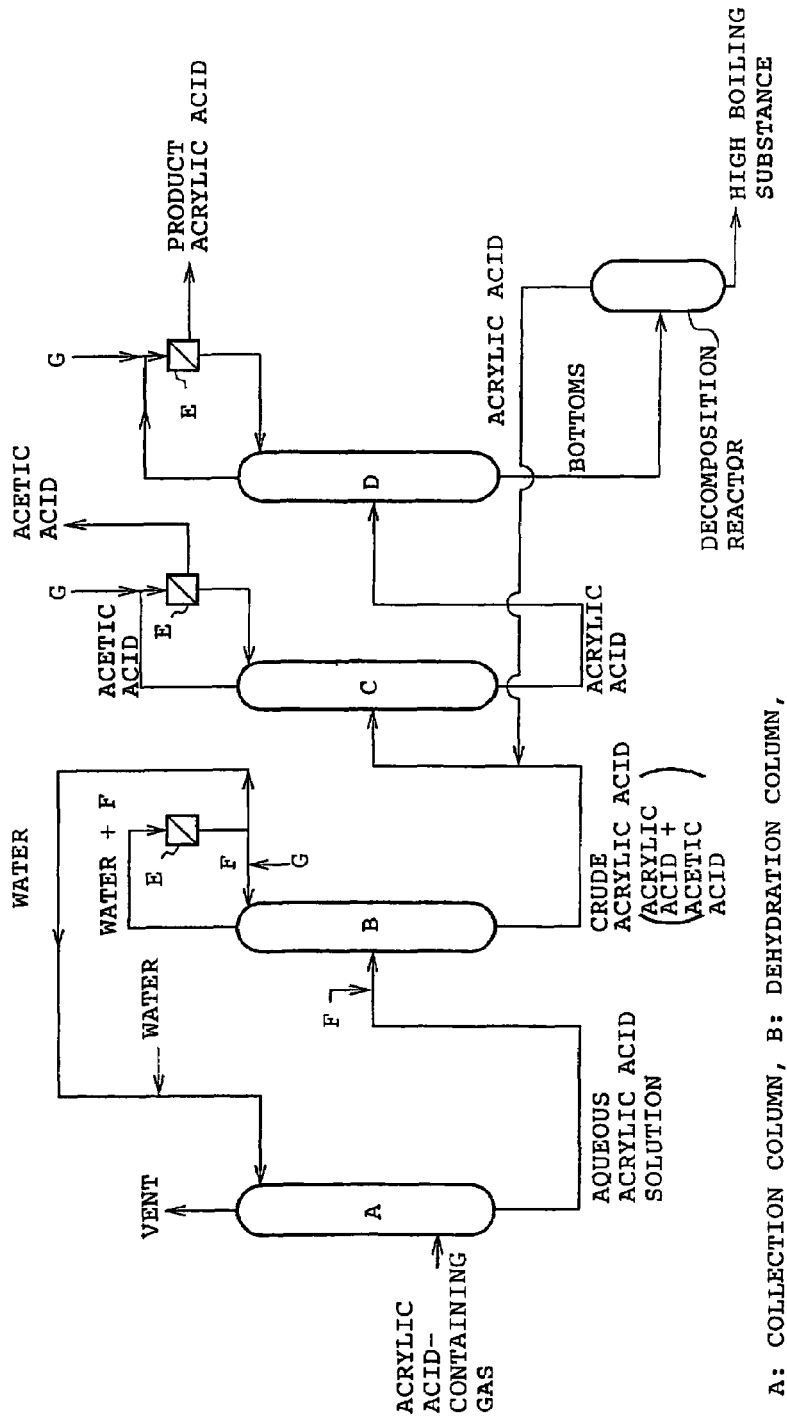
FIG. 1 is a system diagram which shows one example of the production process of acrylic acid.
Figure 2:
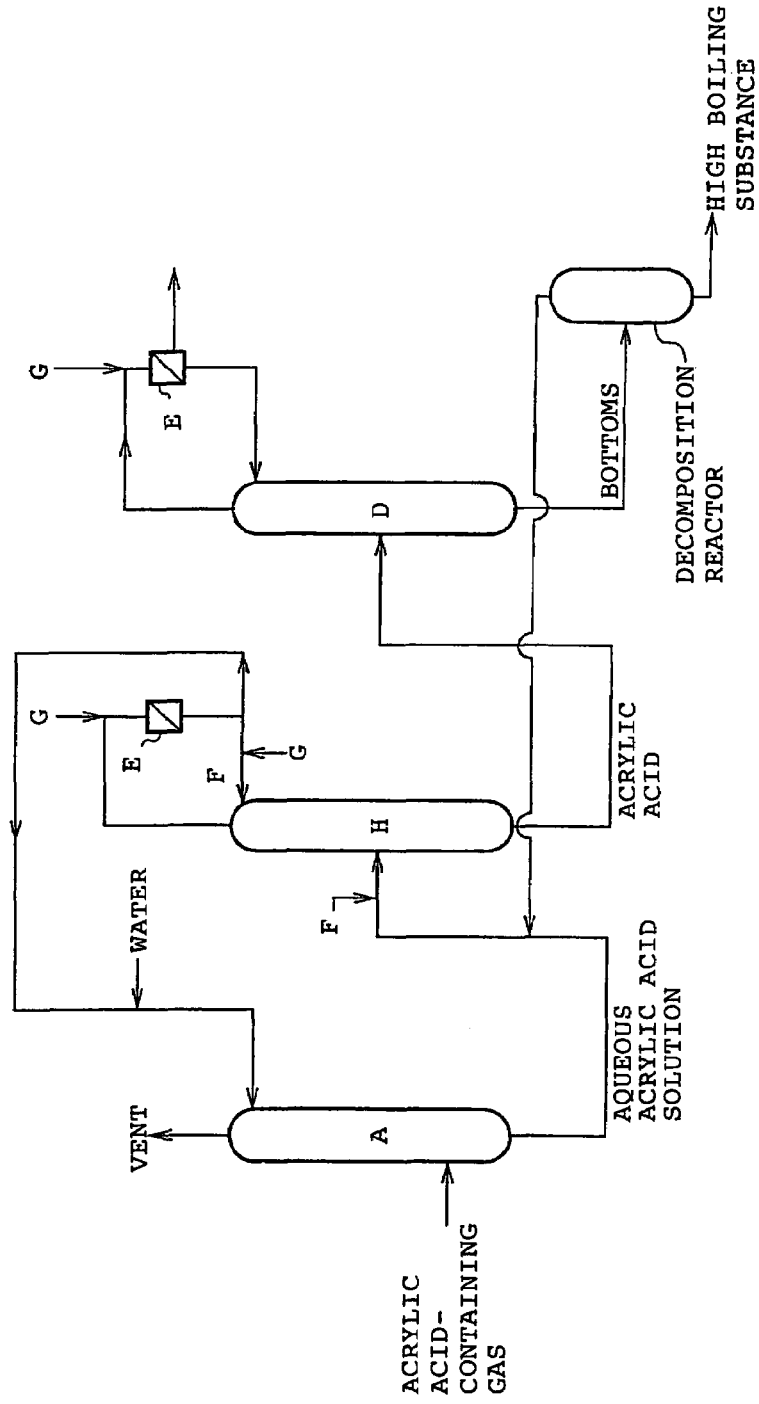
FIG. 2 is a system diagram which shows another example of the production process of acrylic acid.

Now, a practical embodiment of the process for producing (meth)acrylic acid of the present invention will be described in detail with reference to the drawings. FIGS. 1 and 2 are system diagrams which show examples of the production process of acrylic acid.

Further, in the following, the process for producing (meth) acrylic acid of the present invention is described in accordance with the process for producing acrylic acid. However, the present invention may be applied to a process for producing methacrylic acid by a vapor-phase catalytic oxidation reaction of isobutylene and/or t-butyl alcohol in entirely the same manner as in the production of acrylic acid. When the present invention is applied to the production of methacrylic acid, the content of β-methacryloxyisobutyric acid in the feed stream fed to a distillation column is controlled instead of that of β-acryloxypropionic acid in the case where the invention is applied to the production of acrylic acid.

The process for producing acrylic acid as the object of the present invention is based on the production process comprising an oxidization step to produce acrylic acid by means of a vapor-phase catalytic oxidation reaction of propane, propylene and/or acrolein as a starting material, a collection step to collect an acrylic acid-containing gas from the oxidization step as an aqueous acrylic acid solution by contacting the acrylic acid with water in the collection column as shown in FIG. 1, a step to separate acrylic acid and water from the aqueous acrylic acid solution by distillation in a dehydration column by employing an azeotropic solvent (azeotropic agent), a step to separate acetic acid as a low boiling point impurity from acrylic acid by distillation in an acetic acid separation column, and further, a step to separate off high boiling point impurities in a fractionating column.

Namely, in the FIG. 1, the acrylic acid-containing gas obtained by the vapor-phase catalytic oxidation by employing molecular oxygen-containing gas of propane, propylene and/or acrolein, is introduced to the collection column of acrylic acid, and then contacted with water to produce the aqueous acrylic acid solution. Here, the above acrylic acid-containing gas contains $N_2$, $CO_2$, acetic acid, water and the like. Portions of acetic acid and water, $N_2$ and $CO_2$ are discharged from the top of the collection column as a vent gas.

The aqueous acrylic acid solution from the collection column is fed to the dehydration column together with an azeotropic agent, an azeotropic mixture comprising-water and the azeotropic agent is distilled from the top of the dehydration column, and acrylic acid containing acetic acid can be obtained from the bottom. The azeotropic mixture comprising water and the azeotropic agent distilled from the top of the dehydration column is led to a storage tank to separate an organic phase mainly comprising the azeotropic agent and an aqueous phase mainly comprising water. A polymerization inhibitor is added to the organic phase, and then recycled to the dehydration column. On the other hand, the aqueous phase is recycled to the collection column for acrylic acid, and then used as collection water to be contacted with the acrylic acid-containing gas. Further, water is supplemented to the water-returning line, as the case requires. Further, in order to recover the azeotropic agent from water in the water returning line, the water may be recycled to the collection column for acrylic acid after it is passed through an azeotropic agent recovery column (not shown in Figs.).

The crude acrylic acid discharged from the bottom of the dehydration column is led to the acetic acid separation column to remove the remaining acetic acid, whereby the acetic acid is separated and removed from the top. The acetic acid removed from the top contains acrylic acid, and there may be a case where the portion is returned to the process.

From the bottom of the acetic acid separation column, acrylic acid can be obtained, in which acetic acid is not substantially contained. The acrylic acid is led to the fractionating column, and then the high boiling point impurities are separated and removed to obtain acrylic acid having high purity as a product. The bottoms of the fractionating column will be led to a decomposition column.

Further, the present invention can be also applied to a process for producing acrylic acid having a step to separate water, acetic acid and a solvent all at once from the aqueous acrylic acid solution by distillation and separation, as shown in FIG. 2, wherein functions of the dehydration column and the acetic acid separation column as shown in FIG. 1 are integrated into one.

Namely, in FIG. 2, the aqueous acrylic acid solution from the collection column is introduced into the distillation column after the azeotropic agent is added thereto. Water, acetic acid and azeotropic products are distilled from the top of the distillation column, the azeotropic products are returned to the distillation column, and water and acetic acid are retuned to the collection column. Acetic acid is discharged out of the system as a vent gas of the collection column. The treatment flow of the bottoms of the distillation column is the same manner as in the treatment flow of the bottoms of the acetic acid separation column in FIG. 1.

Further, the present invention is applicable to a process for producing acrylic acid, which includes a step of extracting acrylic acid from an aqueous acrylic acid solution by using a extraction solvent such as methyl isobutyl ketone, isopropyl acetate, methyl ethyl ketone or toluene, and then distillating and separating the extraction solvent in the acrylic acid extracted and the remaining water, or a process for producing acrylic acid, which has a step of decomposing the Michael addition product by-produced in the process for producing acrylic acid, a step of further distilling and purifying acetic acid separated by distillation, a step of further distilling the aqueous fraction separated by distillation to recover e.g. the solvent, or an additional purification step of producing acrylic acid having high purity.

In the present invention, the concentration of β-acryloxypropionic acid is controlled in the feed stream in every distillation column to be subjected to the above purification of acrylic acid. The feed stream in the distillation column, of which the main purpose is to separate water and acrylic acid, to separate acetic acid and acrylic acid, or to separate water, acetic acid, an azeotropic solvent and acrylic acid, may, for example, be mentioned. Further, when there are two or more feed streams, the total composition thereof is to be treated as prescribed by the present invention.

With respect to the control of the concentration of β-acryloxypropionic acid contained in the feed stream, the relative value of the concentration by mass to the concentration of acrylic acid in the feed stream is to be controlled. The specific controlled value of the ratio in concentration by mass (hereinafter sometimes simply referred to as "relative concentration") of β-acryloxypropionic acid to acrylic acid, is at most one-fiftieth, more preferably at most one-sixtieth, in the distillation column, of which the main purpose is to separate water and acrylic acid. In the distillation column, of which the main purpose is to separate acetic acid and acrylic acid, it is at most one-fortieth, more preferably at most one-fiftieth. Further, in the distillation column, of which the main purpose is to separate water, acetic acid, an azeotropic solvent and acrylic acid, it is at most one-fiftieth, more preferably at most one-sixtieth.

The method for measuring the concentration by mass of β-acryloxypropionic acid and acrylic acid, is not particularly limited, but the method of using gas chromatography may be convenient and preferred. (Hidezo Omori: Acrylic Acid and Polymer Thereof [I]: published by Shokodo Co. Ltd.)

The specific method for producing acrylic acid by controlling the relative concentration of β-acryloxypropionic acid in the feed stream of the distillation column followed by maintaining the value within the controlled value of the present invention, is not particularly limited, but a few examples will be mentioned as follows. Firstly, the method for controlling the production itself of β-acryloxypropionic acid may be mentioned. For example, the process may be designed so as to lower the temperature as far as possible at the portion where acrylic acid is present and to minimize the retention time. Specifically, a method of maintaining the operation temperature low by lowering the design operation pressure of the distillation column, a method of lowering the design storage temperatures in tanks, and a method of decreasing the retention time by designing e.g. the hold-up volume, the bottom volume or the tank volume in the distillation column to be small as far as possible, may, for example, be mentioned. Further, in the actual operation, there is a method of e.g. controlling the operation temperature or the liquid level to minimize the retention time of the liquid e.g. at the bottom of the distillation column or in the tank.

If the relative concentration of β-acryloxypropionic acid does not satisfy the prescribed controlled value, the operation condition is changed immediately so as to satisfy the controlled value. To change the operation condition to decrease the relative concentration of β-acryloxypropionic acid, the operation load may be increased, the operation pressure may be lowered in the distillation column, the quench column or the like, or the controlled liquid level in tanks or vessels may be lowered. Further, a control method may be included wherein guidelines for the operation conditions are set so as to satisfy the controlled value all the time, by grasping the tendency with time.

Further, the present invention includes a case of a non-steady operation, e.g. at the time of trouble or startup. At the time of such non-steady operation, it is required to tentatively store the process fluid in e.g. a buffer tank, an off specification tank or a rundown tank, and a method for controlling the storage temperature and the storage period in such a tank is also included.

However, in a case where a 80% aqueous acrylic acid solution is stored at a temperature of 40° C., 0.25% of β-acryloxypropionic acid will be formed upon expiration of only 1 day (Hidezo Omori: Acrylic Acid and Polymer Thereof [I]: published by Shokodo Co. Ltd.). After 20 days, β-acryloxypropionic acid in an amount of one-twenty fifth of that of acrylic acid, will be formed. Thus, even the increased portion exceeds the controlled value to a large extent. As such, the value of the storage liquid in the tank at the time of non-steady operation or maintenance tends to readily exceed the controlled value, and the operation control has to be strengthened to satisfy the controlled value particularly when the storage liquid in the tank containing a large amount of β-acryloxypropionic acid thereof is treated at the time of restart-up. Specifically, the concentrations of acrylic acid and β-acryloxypropionic acid in the usual stream and in the storage liquid, are measured by gas chromatography, and the treating amount of the storage liquid is calculated so as to adjust the relative concentration to be controlled of β-acryloxypropionic acid in the feed stream of the distillation column to be at most the controlled value, and the control is carried out based on this result.

Further, in the present invention, the above rundown tank and the off specification tank are employed so as to store the process liquid which was present inside of the plant and contains a valuable substance formed, when the plant operation is suspended for the use of the plant or in order to recover a valuable substance at the time of next operation. Further, the buffer tank is employed so as to prevent the influence of the operation change on the upstream side over the downstream side by tentatively storing the feed stream to the next device discharged from a device such as the distillation column.

As a method for feedback control of the operation conditions such as the respective flow volumes, temperatures, or pressures based on the above-mentioned gas chromatography analysis and the result thereof, an off-line analysis, an on-line autoanalysis, a manual control, an on-line automatic control etc. may be suitably carried out in combination. Further, the concentration by mass of acrylic acid dimmer in the off specification tank is preferably at most 5%, although the reason is not clearly understood.

Further, if the process of the present invention is carried out in combination with a conventional polymerization inhibiting technique of acrylic acid, the undesirable polymerization reaction in the purification step of acrylic acid can be suppressed more effectively, such being preferred. In such a case, the conventional method which may be used, is not particularly limited. However, it may, for example, be represented by a method of adding an inhibitor air to the distillation column together with, as a polymerization inhibitor, a phenol type polymerization inhibitor such as hydroquinone; an amine type polymerization inhibitor such as phenothiazine, a phenylene diamine or an n-oxyl compound; or a metal salt type polymerization inhibitor such as copper dialkyldithiocarbamate or copper acrylate. Further, it is preferred to minimize a factor which brings about undesirable polymerization reaction of acrylic acid, such as a high temperature portion, a long retention time portion, a retention portion (dead space), a protrusion or the like, whereby the effect of the present invention may be further improved.

According to the present invention, by controlling the relative concentration of an adduct of two molecules of (meth)acrylic acid in the step of distillation and purification for producing (meth)acrylic acid, undesirable polymerization reactions of (meth)acrylic acid in the step of distillation and purification can be suppressed, and troubles such as clogging of devices can be avoided, whereby it is possible to accomplish a continuous operation in a stabilized condition. The possible period of the continuous operation is usually at least 1 month, preferably at least 6 months, more preferably at least 1 year.

Now, the present invention will be described in further detail with reference to Examples and Comparative Examples. However, it should be understood that the present invention is by no means limited to such Examples unless it exceeds beyond its gist.

EXAMPLE 1

The distillation and purification of acrylic acid was carried out in accordance with the present invention, by using a distillation (dehydration) column having a diameter of 1000 mm, which had a reboiler at the bottom and a condenser at the top of the column, the condenser having an outlet connected to a vacuum device and which was provided with 30 plates of ripple trays inside the column.

The average composition of an aqueous acrylic acid solution to be used as a raw material for distillation comprised 55% of acrylic acid, 1.5% of acetic acid, 0.1% of β-acryloxypropionic acid, and the rest being almost water, and the aqueous acrylic acid solution was supplied to the 16th tray at a rate of 1000 kg per hour on average. Toluene was used as an azeotropic solvent to be used with water, and it was refluxed to the 30th tray at a rate of 3100 kg per hour to carry out the operation of the dehydration column. The top pressure of the dehydration column was controlled to be 15.3 kPa. And from the top of the column, phenothiazine and hydroquinone, as polymerization inhibitors, were supplied so that the respective concentrations in the bottom liquid were adjusted to be 500 and 800 ppm, respectively. From the bottom of the column, air was supplied at a rate of 500 L per hour. After 6 hours and after the distillation column was stabilized to be in the constant operation state, an off specification tank storage liquid comprising, by mass concentration, 75% of acrylic acid, 5% of β-acryloxypropionic acid and the rest being toluene, acetic acid and water, was supplied at a rate of 200 kg per hour on average. By setting such a flow rate condition, the controlled concentration of β-acryloxypropionic acid to acrylic acid in the feed stream to the dehydration column becomes as set to be one-sixty forth.

The concentrations of acrylic acid and β-acryloxypropionic acid in the feed stream to be fed to the dehydration column were measured once per day by gas chromatography, and the amount of the tank storage liquid supplied from the tank to the dehydration column, was controlled to maintain the set value, as the case requires.

On the basis of such a controlled method, a continuous distillation operation was carried out for 1 month at the top temperature of 44° C., whereby no increase in the pressure difference in the column (the pressure difference between the top and the bottom) was observed. Further, during this period, the storage tank was controlled to be at a temperature of 15° C., whereby the increase with time of β-acryloxypropionic acid in the tank storage liquid was little, and the concentration by mass was increased only to 5.2%. Further, during this period, the concentration by mass of β-acryloxypropionic acid to acrylic acid in the feed stream fed to the dehydration column was analyzed by means of gas chromatography, and as a result, it was practically controlled to be from one-sixty second to one-sixty fifth.

COMPARATIVE EXAMPLE 1

A continuous distillation operation of the dehydration column was carried out for 1 month by the same apparatus and in the same pressure conditions as in Example 1 except that in Example 1, the amount of the aqueous acrylic acid solution as the distillation raw material, supplied to the dehydration column was changed to 900 kg per hour on average, and the amount of the off specification tank storage liquid supplied was changed to 300 kg per hour on average. Further, the storage tank was controlled to be at 15° C. in the same manner as in Example 1.

As a result, upon expiration of 1 month from the beginning of the operation, an increase by 0.7 kPa in the pressure difference in the column was observed. The concentration by mass of β-acryloxypropionic acid to acrylic acid in the feed stream to the dehydration column during this period was analyzed by means of gas chromatography, and as a result, it was practically controlled to be from one-forty second to one-forty eighth.

EXAMPLE 2

An operation of an acetic acid separation column was continuously carried out following the dehydration and distillation in Example 1, to separate acetic acid from acrylic acid by using the bottoms of the dehydration column in Example 1 as a raw material, wherein, as the acetic acid separation column, a plate distillation column (30 plates) which had a reboiler at the bottom and a condenser at the top of the column, the condenser having an outlet connected to a vacuum device, was connected directly with the dehydration column in Example 1. The average composition of the raw material liquid (bottoms of dehydration column) comprised, by mass concentration, 93.3% of acrylic acid, 2.7% of acetic acid and 2.0% of β-acryloxypropionic acid, and the liquid was supplied to the 15th tray of the acetic acid separation column at a rate of 741 kg per hour on average. The top pressure of the acetic acid separation column was controlled to be 8.0 kPa. And from the top of the column, phenothiazine and hydroquinone, as polymerization inhibitors, were supplied so that the concentrations in the bottom liquid would be 700 and 1000 ppm, respectively. From the bottom of the column, air was supplied at a rate of 300 L per hour. By setting such a condition, the controlled concentration of β-acryloxypropionic acid to acrylic acid in the feed stream to the acetic acid separation column becomes as set to be one-forty sixth.

The concentrations of acrylic acid and β-acryloxypropionic acid in the feed stream were analyzed once per day by gas chromatography. If the concentration was out of the set value, it was controlled by the method of changing the controlled value of the liquid level of the dehydration column on the upstream side, and the continuous distillation operation was carried out for 1 month at the top temperature of 55° C. and reflux ratio of 2.0, whereby no increase in the pressure difference in the column of the acetic acid separation column was observed. During this period, the concentration by mass of β-acryloxypropionic acid to acrylic acid in the feed stream to the acetic acid separation column was analyzed by means of gas chromatography, and as a result, it was practically controlled to be from one-forty fourth to one-forty seventh.

COMPARATIVE EXAMPLE 2

A continuous distillation operation of the acetic acid separation column was continuously carried out for 1 month in the dehydration column in Comparative Example 1 under the same pressure and reflux ratio conditions as in Example 2 except that the same apparatus as in Example 2 was connected directly with the dehydration column in Comparative Example 1, and the bottoms of the dehydration column in Comparative Example 1 was used as a raw material. The average composition of the raw material liquid (bottoms of dehydration column) comprised, by concentration by mass, 93.3% of acrylic acid, 2.7% of acetic acid and 2.6% of β-acryloxypropionic acid, and the liquid was supplied to the acetic acid separation column at a rate of 767 kg per hour on average. Upon expiration of 1 month from the beginning of the operation, an increase by 0.5 kPa in the pressure difference in the column was observed. During this period, the concentration of β-acryloxypropionic acid to acrylic acid in the feed stream to the acetic acid separation column was analyzed by means of gas chromatography, and as a result, it was practically found to be from one-thirty third to one-thirty ninth.

COMPARATIVE EXAMPLE 3

A continuous operation of the dehydration column was carried out for 1 month by the same apparatus and conditions as in Example 1 except for the composition of the distillation raw material liquid and the compositions of the tank storage liquid.

The average composition of the aqueous acrylic acid solution used as the distillation raw material liquid, comprised, by concentration by mass, 55.2 of acrylic acid %, 1.5% of acetic acid and 0.1% of β-acryloxypropionic acid and the rest being mostly water. The initial composition of the tank storage liquid comprised, by concentration by mass, 76% of acrylic acid and 5% of β-acryloxypropionic acid. By setting such a flow rate condition, the controlled concentration of β-acryloxypropionic acid to acrylic acid in the feed stream to the dehydration column was found to be one-sixty forth. Further, the temperature of the storage tank was from 25 to 35° C., when left to chance without any controls.

The continuous distillation operation was carried out for 1 month at the top temperature of the dehydration column of 44° C., whereby no increase in the pressure difference in the column was observed for the initial period of two weeks. However, after that, the pressure difference started to rise, and the rate of rise gradually increased, and after 1 month, an increase by 1.0 kPa in the pressure difference was observed. Here, no temperature control of the storage tank was carried out, whereby when the composition of the storage liquid of the tank after 1 month was measured by means of gas chromatography, it was found that the concentration of β-acryloxypropionic acid increased to 9.2%. This means that the concentration of β-acryloxypropionic acid to acrylic acid in the feed stream to the dehydration column increased to one-thirty sixth.

As described above in detail, according to the process for producing (meth)acrylic acid of the present invention, it is possible to control the undesired polymerization reaction of (meth)acrylic acid in the step of distillation and purification of (meth)acrylic acid, to avoid a trouble such as clogging of devices, and to carry out a constant continuous operation for a long period of time.

The entire disclosure of Japanese Patent Application No. 2002-020328 filed on Jan. 29, 2002 including specification, claims, drawings and summary is incorporated herein by reference in its entirety.

What is claimed is:

1. A process for producing (meth)acrylic acid, which comprises the step of feeding a feed stream of crude (meth) acrylic acid obtained by vapor phase catalytic oxidation to a distillation column mainly for the separation of (meth) acrylic acid and acetic acid, to separate acetic acid from (meth)acrylic acid, wherein the concentration by mass of the adduct of two molecules of (meth)acrylic acid present in the feed stream to the distillation column is controlled to be at most one-fortieth of the concentration by mass of (meth) acrylic acid in the feed stream.

2. A process for producing (meth)acrylic acid which comprises the step of feeding a feed stream of crude (meth) acrylic acid obtained by vapor phase catalytic oxidation, to a distillation column mainly for the separation of water and (meth)acrylic acid, to separate water from the (meth)acrylic acid, wherein the concentration by mass of the adduct of two molecules of (meth)acrylic acid in the feed stream to the distillation column is controlled to be at most one-fiftieth of the concentration by mass of (meth)acrylic acid in the feed stream and, wherein the feed stream contains a liquid of an off specification tank.

3. The process for producing (meth)acrylic acid according to claim 2, wherein the concentration by mass of the adduct of two molecules of (meth)acrylic acid in the off specification tank is at most 5%.

4. The process for producing (meth)acrylic acid according to claim 1, wherein the feed stream contains a liquid of an off specification tank.

5. The process for producing (meth)acrylic acid according to claim 4, wherein the concentration by mass of the adduct of two molecules of (meth)acrylic acid in the off specification tank is at most 5%.

6. The process for producing (meth)acrylic acid which comprises the step of feeding a feed stream of crude (meth)

acrylic acid obtained by vapor phase catalytic oxidation to a distillation column mainly for the separation of water, acetic acid and a solvent, and (meth)acrylic acid, to separate water, acetic acid and the solvent from the (meth)acrylic acid, wherein the concentration by mass of the adduct of two molecules of (meth)acrylic acid in the feed stream to the distillation column is controlled to be at most one-fiftieth of the concentration by mass of (meth)acrylic acid in the feed stream, wherein the feed liquid contains a liquid of an off specification tank.

7. The process for producing (meth)acrylic acid according to claim 6, wherein the concentration by mass of the adduct of two molecules of (meth)acrylic acid in the off specification tank is at most 5%.

8. A process for producing (meth)acrylic acid from a (meth)acrylic acid-containing gas obtained by vapor-phase catalyst oxidation, comprising the step of contacting the gas with water in a collection column to obtain an aqueous (meth)acrylic acid solution, the step of recovering crude (meth)acrylic acid from the aqueous (meth)acrylic acid solution by feeding the aqueous (meth)acrylic acid solution to a distillation column mainly for the separation of water and (meth)acrylic acid, to separate water from the aqueous (meth)acrylic acid solution to obtain a crude (meth)acrylic acid containing as impurities acetic acid and an adduct of two molecules of (meth)acrylic acid, wherein the concentration by mass of the adduct of two molecules of (meth) acrylic acid in the feed stream to the distillation column is controlled to be at most one-fiftieth of the concentration by mass of (meth)acrylic acid in the feed stream, and the succeeding step of feeding the crude (meth)acrylic acid to a distillation column mainly for the separation of (meth) acrylic acid and acetic acid, to separate acetic acid from the (meth)acrylic acid, wherein the concentration by mass of an adduct of two molecules of (meth)acrylic acid in the feed stream to the distillation column is controlled to be at most one-fortieth of the concentration by mass of (meth)acrylic acid in the feed stream.

* * * * *